US006974698B1

(12) United States Patent  (10) Patent No.: US 6,974,698 B1
Miller et al.  (45) Date of Patent: Dec. 13, 2005

(54) METHODS FOR DELIVERING BIOLOGICALLY ACTIVE MOLECULES INTO CELLS

(75) Inventors: Jeffery L. Miller, Potomac, MD (US); Urszula Wojda, Warsaw (PL); Paul K. Goldsmith, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/483,434

(22) Filed: Jan. 14, 2000

Related U.S. Application Data

(60) Provisional application No. 60/116,240, filed on Jan. 15, 1999.

(51) Int. Cl.[7] .................................................. C12N 5/02
(52) U.S. Cl. ...................... 435/375; 435/455; 536/23.1
(58) Field of Search ...................... 536/23.1; 435/455, 435/468, 471

(56) References Cited

U.S. PATENT DOCUMENTS

| 4,996,142 | A | * | 2/1991 | Al-Hakim et al. | 435/6 |
| 5,108,921 | A | | 4/1992 | Low et al. | 435/375 |
| 5,254,342 | A | | 10/1993 | Shen et al. | 424/401 |
| 5,766,902 | A | | 6/1998 | Craig et al. | 435/461 |
| 6,045,795 | A | * | 4/2000 | Ulevitch et al. | 424/154.1 |

OTHER PUBLICATIONS

Karlsson, et al. APMIS. 1992, Suppl.27, vol. 100, pp. 71-83.*
Keusch, Gerald. Reviews of Infectious Diseases. 1979, vol. 1, No. 3, pp. 517-529.*
Hermanson, G.T. Bioconjugate Techniques. 1996, Academic Press, Inc. pp. 3-136, 371-401, 570-571, 575-584 and 590-592.*
Palu, et al. Journal of Biotechnology, 1999, vol. 68, pp. 1-13.*
Luo, et al. Nature Biotechnology, Jan. 2000, vol. 18, pp. 33-37.*
Verma, et al. Nature, 1997, vol. 389, pp. 239-242.*
Wojda, et al. Molecular Biology of the Cell, Nov. 1997, vol. 8, No. Suppl., p86A.*
Dachs et al. Oncology Research. 1997, vol. 9, pp. 313-325.*
Schwartzenberger, et al. Journal of Virology. 1997, vol. 71, No. 11, pp. 8563-8571.*
Spear, et al. Heparin and Related Polysaccharides. D.A. Lane editor, Plennum Press, 1992, pp. 341-353.*
Baker, A., M. Saltik, H. Lehrmann, I. Killisch, V. Mautner, G. Lamm, G. Christofori, M. Cotten, "Polyethylenimine (PEI) is a simple, inexpensive and effective reagent for condensing and linking plasmid DNA to adenovirus for gene delivery." *Gene Therapy* 4:773-782 (1997).
Ferro, W.G., S. Li, J.D. Rosenblatt, N. Sirianni, J.E. Morgan, T.A. Partridge, L. Huang, E.P. Hoffman, "Selection and use of ligands for receptor-mediated gene delivery to myogenic cells." *Gene Therapy* 4:664-674 (1997).
Franco, Robert S., J. Lohmann, E. B. Silberstein, G. Mayfield-Pratt, M. Palascak, T. A. Nemeth, C. H. Joiner, M. Weiner, D. L. Rucknagel, "Time-dependent Changes in the Density and Hemoglobin F. Content of Biotin-Labeled Sickle Cells." *The Journal of Clinical Investigation* 101 No. 12:2730-2740 (1998).
Kircheis, R., Kichler, A., Wallner, G. M. Kursa, M. Ogris, T. Felzmann, M. Buchberger and E. Wagner, "Coupling of cell-binding ligands to polyethylenimine for targeted gene delivery." *Gene Therapy* 4:409-418 (1997).
Kukowska-Latallo, J.F., A. U. Bielinska, J. Johnson, R. Spindler, D. A. Tomalia, J. R. Baker, Jr., "Efficient transfer of genetic material into mammalian cells using Starburst polyamidoamine dendrimers." *Genetics* 93:4897-4902 (May 1996).
Schoeman, R., D. Joubert, M. Ariatti, A. O. Hawtrey, "Further Studies on Targeted DNA Transfer to Cells Using a Highly Efficient Delivery System of Biotinylated Transferrin and Biotinylated Polylysine Complexed to Streptavidin." *Journal of Drug Targeting* 4:509-516 1995).
Youssoufian, H., F. A.E. Kruyt, Xiaotong Li, "Protein Replacement by Receptor-Mediated Endocytosis Corrects the Sensitivity of Fanconi Anemia Group C Cells to Mitomycin C." *Blood* 93:363-369 No. 1 (Jan. 1, 1999).
Zanta, M.A., O. Boussif, A. Adib, J.P. Behr, "In Vitro Gene Delivery to Hepatocytes with Galactosylated Polyethylenimine." *Bioconjugate Chem.* 8:839-844 (1997).

* cited by examiner

*Primary Examiner*—James Ketter
*Assistant Examiner*—Patrick S. Riggins
(74) *Attorney, Agent, or Firm*—Needle & Rosenberg, PC

(57) ABSTRACT

Methods for delivering a biologically active molecule into a cell by linking a molecule to the cell surface, wherein the molecule can act as a surface receptor, then complexing the biologically active molecule with a ligand for the surface receptor, and finally contacting the biologically active molecule-ligand complex with the cell surface are disclosed. Delivery of any biologically active molecule, e.g. proteins, enzymes, nucleic acids, hormones, nucleic acids, and oligonucleotides, is contemplated. The use of biotin or biotinylated antibodies as the surface receptor is disclosed. The use of PEI and PEI-avidin conjugates complexed with oligonucleotides for delivery into a directly or indirectly biotinylated cell surface, along with the PEI-avidin-nucleic acid compositions, are disclosed. Primary and cultured cells with a covalently linked surface receptor molecule, such as biotin, on their surfaces are also disclosed.

3 Claims, 1 Drawing Sheet

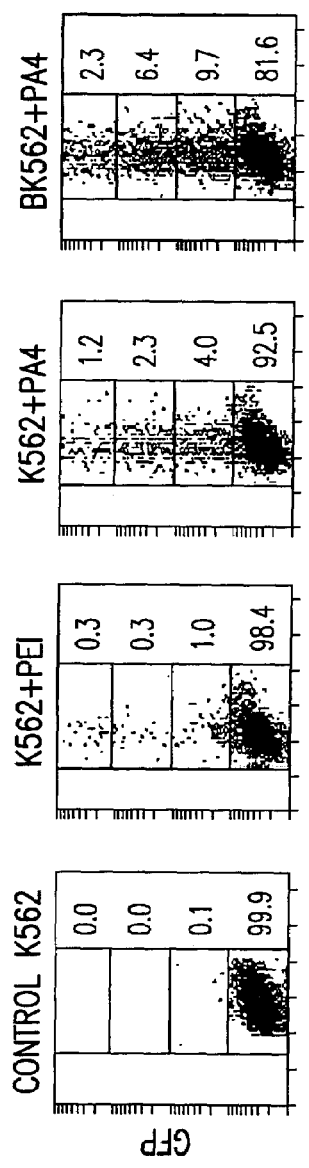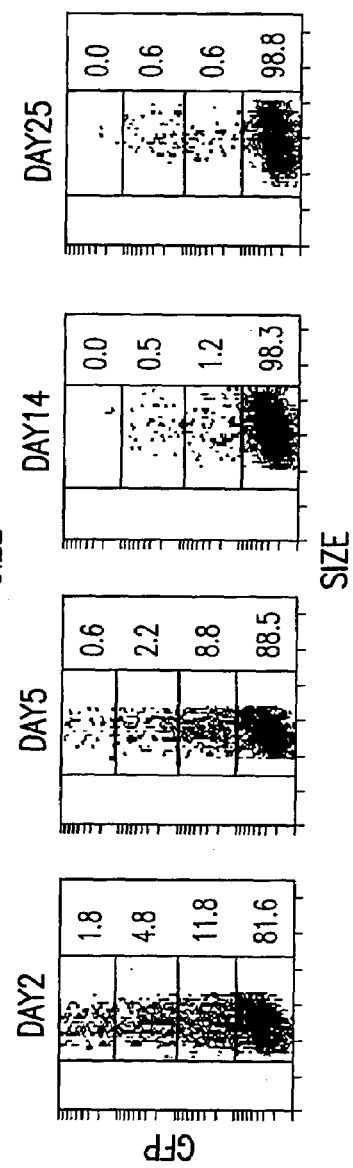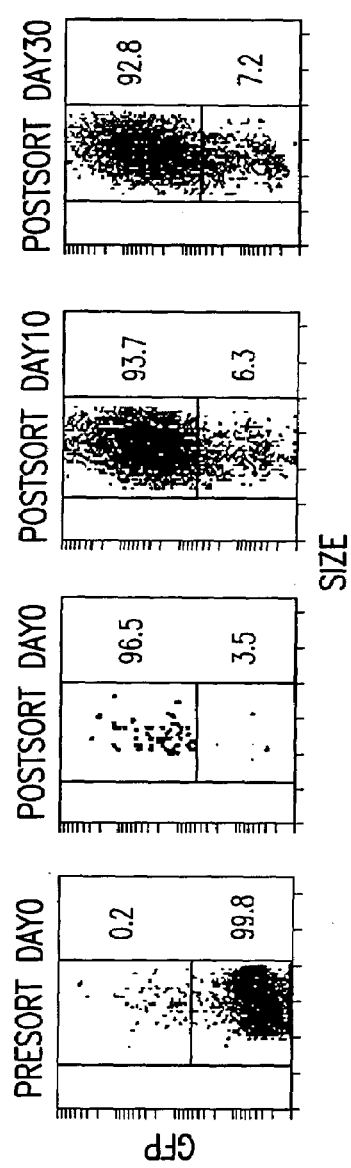

METHODS FOR DELIVERING BIOLOGICALLY ACTIVE MOLECULES INTO CELLS

This application claims benefit to Provisional Application 60/116,240, filed Jan. 15, 1999.

FIELD OF THE INVENTION

This invention is in the field of methods and compositions for delivering biologically active molecules into cells.

BACKGROUND OF THE INVENTION

With the rapid increase in knowledge of the cellular mechanisms and processes that lead to disease or that are disrupted by genetic mutations, scientists can envisage potential solutions that involve the delivery of molecules into a cell that can then affect a change in a mechanism or process for therapeutic or prophylactic value. For example, several technologies to deliver nucleic acids, particularly DNA, into a cell have been described. Researchers have identified at least three requirements for accomplishing DNA delivery: 1) DNA has to be in a form that will associate with the cell membrane and be taken up by the cell; 2) the DNA has to be coupled with a molecule that is targeted to the correct types of cells, and 3) the DNA has to move into the cell compartments where it can exert a desired biological effect.

To address the first requirement, cationic lipid vectors have been developed during the last decade. Cationic vectors are a class of macromolecules that enhance the delivery of DNA by virtue of their positive charge. The cationic charge of the lipids causes an electrostatic affinity of derived liposomal preparations for the DNA and the cell membrane. Polylysine and other cationic peptides have also been developed in order to condense the DNA, but their overall efficiency relies on facilitation of the transferred DNA release from endosomal compartments (Plank, C. et al. 1994, J. Biol. Chem. 269:12918–12924; Gottschalk, S. et al. 1996, Gene Ther. 3:48–57). To address the first and third requirements, another polycationic vector, polyethylenimine (PEI), has recently gained favor due to its intrinsic endosomolytic properties. Every third backbone atom of PEI is an amino nitrogen providing exceptionally high pH buffering capacity. In the endosome, PEI acts as an efficient "proton sponge" probably triggering osmotic swelling and disruption of endosomal vesicles which promotes efficient gene transfer demonstrated in vitro (Boussif, O., et al. 1995. Proc. Natl. Acad. Sci. U.S.A. 92: 7297–7301) and in vivo (Abdallah, B., et al. 1996. Hum. Gene Ther. 7:1947–1954).

However, improved targeting strategies, to address the second requirement, have been required to improve the overall efficiency of PEI among nonadherent cells (Boussif, O., et al., ibid.). Thus, each generation of cationic vectors has evolved from experimental data gained from related vectors. The efficiency of several vector classes has been improved by enhancing attachment to specific plasma membrane receptors. Those receptors are usually selected due to their naturally high abundance on the targeted cell types. The recent description of several viral vector receptors has led to strategies aimed at the manipulation of viral tropism including viral pseudotyping (Kasahara, N., et al. 1994, Science 266:1373–1376). However, the production of clinical grade virions remains arduous. Conversely, attempts have been made to artificially express viral receptors on human cells in order to increase transfer efficiencies (Bertran, J. et al. 1996, J. Virol. 70:6759–6766). Similar adaptation of lipid and polymeric vectors has been accomplished by conjugating them to ligands for known target cell receptors. While these lipid and bioconjugate vectors are relatively simple to prepare, their stability in vivo and transfection efficiency in primary cells remains low. Asialoglycoprotein receptors expressed at high levels exclusively on hepatocytes have been used in gene delivery studies (Zanta, M. A. et al. 1997, Bioconjug. Chem. 8:839–844). Folate receptors on neoplastic cells have been used for decades for the delivery of therapeutic folate analogs. Delivery of DNA to cancer cell lines via these folate receptors has been demonstrated, but transfection is limited to cells expressing the receptor at high levels (Dachs, G. U., et al. 1997, Oncol. Res. 9:313–325). The same concept of targeting highly expressed receptors has been successfully applied to the incorporation of transferrin into bioconjugates. Binding of transferrin to rapidly growing cells leads to its clustering in coated pits and eventual transfer into the cytoplasm (Schwarzenberger, P., et al. 1997, J. Virol. 71:8563–8571). In addition to natural ligands for cell surface receptors, monoclonal antibodies directed against highly expressed surface receptors have been incorporated into the design of bioconjugates (Poncet, P., et al. 1996 Gene Therapy 3:731–738). While these techniques for receptor-targeted gene delivery hold great promise, the broad application of the concept is limited by the need to develop a distinct vector for each receptor and the inevitable reliance on naturally occurring receptor molecules which are often expressed at an inadequate level on primary cells, which will be a major target for therapies. Since there is a clear correlation between the number of membrane receptors and transfection efficiency, it is an as yet elusive goal to increase the number of receptors on the cell surface as much as possible.

Thus, there is a need for a method to introduce new receptors or, alternatively to increase the number of receptors, on nucleated cells so that they can become efficient targets for delivery of therapeutic, prophylactic or diagnostic molecules. There is further a need for a universal ligand-mediated system, so that a wide range of therapeutic, prophylactic or diagnostic molecules can be delivered through the same receptor.

BRIEF DESCRIPTION OF THE FIGURES

FIG. 1 (Panels A–C) presents flow cytometry analyses of K562 cells, native and biotinylated, which are transfected with plasmid DNA encoding green fluorescent protein (GFP). The analysis divides the cells into four response decades, corresponding to cells not expressing GFP, and cells expressing GFP at a low, medium and high level (the percentage of cells in each fluorescence decade is marked on the right side of each box). (A) shows the cell distribution 48 hours after transfection for K562 cells transfected with a GFP-PEI complex ("K562+PEI"), K562 cells transfected with a GFP-PEI-avidin complex ("K562+PA4"), and biotinylated K562 cells transfected with a GFP-PEI-avidin complex ("BK562+PA4"), compared to nontransfected K562 cells ("control K562"). (B) shows biotinylated K562 cells transfected with a GFP-PEI-avidin complex and analyzed 2, 5, 14, and 25 days after transfection in cell culture. (C) shows biotinylated K562 cells transfected with a GFP-PEI-avidin complex, sorted 30 days following transfection, with the sorted GFP-expressing cell population cultured for an additional 30 days, and analyzed by flow cytometry 0, 10, and 30 days after sorting. The relative GFP expression is shown on the y-axis with positive transfectants defined as those cells fluorescing at levels $\geq 2$ standard deviations above the control values.

DETAILED DESCRIPTION OF THE INVENTION

Definitions:

"Bioconjugate" as used herein is a biologically active molecule linked to a ligand or a ligand conjugate.

"Biologically active molecule" means a molecule that, when introduced into a cell, can affect processes or reactions occurring within a cell.

"Oligonucleotide" means a synthetic single-stranded or double-stranded nucleic acid of at least 5 nucleotides. In the case of double stranded oligonucleotides, one strand may be the complementary ribonucleic acid (RNA), thus making an RNA-DNA hybrid.

"Primary cell" means a cell of a living organism, which is not immortalised, and which is present in the organism (in vivo) or is removed from the organism for treatment or manipulation (ex vivo).

"Primary cell culture" means the cells taken from a tissue source and their progeny grown in culture before subdivision and transfer to a subculture.

"Surface receptor", as used herein, means a molecule covalently bound to a cell surface, which can function as a receptor by interacting, at a high affinity, to a ligand, wherein the covalently linked molecule is not naturally expressed on the cell surface. The surface receptor can alternatively be a molecule that is expressed only at low levels on the cell surface.

DETAILED DESCRIPTION

The invention claimed herein provides a method for delivering a biologically active molecule into a cell comprising: 1) covalently linking a molecule to the cell surface, wherein the molecule can act as a surface receptor, 2) complexing the biologically active molecule with a ligand for the surface receptor, and 3) contacting the biologically active molecule-ligand complex with the cell surface. As defined herein, a biologically active molecule is one or more molecules which can, upon entering a cell, affect cellular metabolism or other cellular activities. Proteins, enzymes, vitamins, vaccines, transcription factors, hormones, carbohydrates, lipids, and nucleic acids (including RNA, DNA, RNA-DNA hybrids, and gene constructs) are examples of biologically active molecules. Oligonucleotides that can bind to RNAs in the cytoplasm or the nucleus, and thereby affect their expression or stability, are also examples of biologically active molecules. Oligonucleotides can be between 5 and 1000 nucleotides long. Typically, oligonucleotides of approximately 10, 20, and 30 nucleotides are used. The oligonucleotides can be nucleic acids that hybridize with other nucleic acids to prevent their replication or transcription, or they can be ribozymes that have catalytic activity on certain nucleic acids. An antibody would not be considered a biologically active molecule. Combinations of the above-described types of biologically active molecules can be delivered into a cell using the methods described herein.

The invention also provides a method for delivering marker molecules into a cell, comprising 1) covalently linking a molecule to the cell surface, wherein the molecule can act as a surface receptor, 2) complexing the marker molecule with a ligand for the surface receptor, and 3) contacting the marker molecule-ligand complex with the cell surface. Fluorescein, beta-galactosidase and beta-glucuronidase are examples of marker molecules. An antibody would not be considered a marker molecule. In the case of enzyme marker molecules, the method further comprises adding the enzyme's substrate to the cell and detecting the product of the enzyme reaction.

The cell targeted for delivery of a biologically active molecule is a nucleated cell that is capable of endocytosis. The cell can be a cultured and immortalized cell, a primary cell in vivo or ex vivo, or a cultured primary cell. One group of cells that can be targeted are the primary peripheral blood mononuclear cells found in blood. Such cells are of several different types, and include fully differentiated, mature cells as well as cells at various stages in the cell division cycle. Cells of the liver, breast, heart, lung, pancreas, kidney and colon are specific targets for this method. Epithelial cells are also targets for the method of this invention. Mammalian cells will be the typical targets of the present methods and compositions; however the methods and compositions can be used in eukaryotic cells generally.

The cell surface is covalently linked to a molecule that can function as a "surface receptor", that is, it can bind a ligand specifically and with high affinity. The surface receptor molecule can be covalently linked to any molecule on the cell surface, such as proteins, glycoproteins, carbohydrates, or lipids. This method of introducing surface receptors to cells makes it possible to target cells without knowledge of their surface phenotype. The techniques for binding one molecule to another molecule anchored in a cell membrane, which often employ cross-linking reagents, are extensive and well-known in the art (for example, see Hermanson, Greg T., 1996, *Bioconjugate Techniques*, Academic Press, Inc.). In a preferred embodiment, the "surface receptor" molecule is biotin, and it is covalently bound to free amino groups on proteins in the cell plasma membrane. Biotin is a preferred surface receptor in this method, since it has a remarkably high affinity for its ligand, avidin $(Ka=10^{15}M^{-1})$, has been extensively studied, and is readily available from commercial sources (Wilchek and Bayer, 1988 *Anal. Biochem.* 171(1):1–32). In another embodiment, a protein, preferably an antibody or a purified receptor from another cell type that is not normally expressed on the target cells, is covalently linked to the cell surface to act as a surface receptor. Alternatively, a molecule that is only expressed at low levels on the target cell is covalently linked to the cell surface to act as a surface receptor. Combination of molecules that are not naturally expressed on the target cell and molecules that are expressed only at low levels on the target cells can be used in the present delivery methods. Examples of such naturally-occurring receptors are transferrin receptors, cytokine receptors, such as the interleukin (IL)-3 receptors, folate receptors and asialoglycoprotein receptors. In a specific embodiment, biotinylated antibodies can act as the surface receptor, allowing the targeting of subpopulations of cells in vivo or ex vivo based on the presence of the antigen for the biotinylated antibody on the surface of the targeted cell.

The ligand for the chosen surface receptor is then complexed, either covalently or non-covalently, directly or indirectly, to the biologically active molecule. The ligand can be a synthetic or naturally occurring molecule. In a specific embodiment in which the surface receptor is an antibody (either polyclonal or monoclonal), the ligand could be the original hapten used to raise the antibody, or any other hapten known to bind to the antibody with high affinity. The ligand must be complexed with the biologically active molecule in a manner that does not impede the functioning of the biologically active molecule in the cell. In one embodiment, the ligand is complexed through a covalent bond that would be cleavable once the complex had been taken up into the cell. Alternatively, in the situation where the ligand does not interfere with the functioning of the biologically active molecule, it will be preferable to create a ligand-biologically active molecule complex that is stable, particularly for in vivo applications.

In preferred embodiments, the ligand is avidin or streptavidin. Avidin can be bound directly to the biologically active molecule, e.g. an enzyme, through the carbohydrate chains on the avidin molecule, thus leaving all biotin binding sites on avidin free to interact with the biotinylated cell surface. Alternatively, avidin can be conjugated to a cationic polymer, such as polyethylenimine, and the resulting avidin-cationic polymer conjugate is then complexed with the biologically active molecule, that is, a polyanion, such as a nucleic acid, an oligonucleotide or a protein, creating a "ligand conjugate-biologically active molecule" complex. In a specific embodiment, polyethylenimine (PEI) is the cationic polymer, and the PEI-avidin conjugates are herein referred to as "PA conjugates". Conjugates of PEI-avidin can be made with increasing amounts of avidin, depending on the particular application. In a specific embodiment, the PA conjugate is complexed with a DNA or an oligonucleotide at a desired ratio of PA to the DNA or the oligonucleotide. The ratio is defined as the molar ratio of PEI nitrogen to nucleic acid phosphate, herein referred to as the N:P ratio, and typical values range from 0.8 to 12.0. For in vivo delivery of PEI-based bioconjugates that are complexed with DNA or oligonucleotides, the N:P ratio should approach electrophoretic neutrality, that is, approximately 4.8 or less, preferably 3.2 or less. Streptavidin can be used interchangeably for avidin in all the methods and compositions of the claimed invention.

The ligand-biologically active molecule complex or the ligand conjugate-biological active molecule complex is then contacted with the surface receptor that was added to the outside surface of the cell. The surface receptor-ligand/ligand conjugate-biologically active molecule complex is endocytosed by the natural processes of the cell. In the Examples provided herein, high affinity binding of the bioconjugate to the surface receptors covalently bound to cell membrane proteins results in efficient endocytosis of those molecules into primary and cultured human nucleated cells.

The Examples herein thus demonstrate that existing surface membrane molecules can be modified by the covalent addition of surface receptors in order to predictably transport biologically active molecules linked to a ligand or a ligand conjugate to the interior of cells. The transport of biologically active molecules using other analogous surface receptor-ligand/ligand conjugate strategies can be accomplished using the techniques described herein. Delivery of therapeutic, prophylactic or diagnostic compounds to the intracellular space and clearance of toxic compounds from the extracellular space are two specific applications for the methods and compositions of the invention. The invention claimed herein obviates the need for knowledge of target cell phenotype to accomplish efficient internalization of biologically active molecules by surface receptor-mediated endocytosis. The techniques for covalently modifying existing surface elements to manipulate endocytosis as described herein are applicable to in situ, ex vivo and in vivo therapies.

For in vivo surface receptor addition, e.g. biotinylation, of cell surfaces in tissues or organs of the body, the surface receptor in a form suitable for administration is introduced into the body so that the desired cells become targeted. Intravenous (IV) treatment will effectively deliver surface receptor to the surfaces of primary blood cells, lungs, and liver, for example. Topical (with or without IV) administration will effectively deliver surface receptor to epithelial cells, for example skin or cervical epithelium. For ex vivo surface receptor addition, e.g. biotinylation of primary nucleated blood cells, techniques known to one skilled in the art can be followed (e.g. Franco, R. S. et al., 1998, *J. Clinical Investigation* 101(12):2730–2740).

The modes of administration of surface receptor will vary predictably according to the tissue being targeted. For many localized pathologic conditions including cancers, infections (e.g., hepatitis, cystitis, proctitis, cervicitis, etc.) as well as precancerous conditions, catheterization of an artery upstream from the organ is a preferred mode of delivery, because it avoids unneeded exposure and binding of surface receptor by the lung and liver.

Leukemias and other abnormalities or diseases of the blood may be more readily treated by ex vivo administration of surface receptor. Ex vivo (excorporeal) delivery can be routinely performed by those skilled in the art (e.g. Wolfe, J T et al. 1994 *Artificial Organs* 18(12): 888–897; Matsuda, Y, et al. 1994, *Artificial Organs* 18(1):93–99).

The surface receptor may be administered topically, parenterally (e.g., intravenously), by intramuscular injection, by intraperitoneal injection, transdermally, excorporeally or the like, although IV or topical administration is typically preferred. Other acceptable modes of administration include intranasal and intraocular routes, inhalation, installation into a body cavity or organ, and implantation. The exact amount of surface receptor required will vary from subject to subject, depending on the species, age, weight and general condition of the subject, the number of cells to be targeted, the number of sites on the cell surface to which the surface receptor is to be added, the particular surface receptor used, its mode of administration, and the like. Thus, it is not possible to specify an exact amount. However, an appropriate amount may be determined by one of ordinary skill in the art using only routine experimentation.

Parenteral administration, if used, is generally characterized by injection. Injectables can be prepared in conventional forms, either as liquid solutions or suspensions, solid forms suitable for solution or suspension in liquid prior to injection, or as emulsions. Topical administration can be by creams, gels, suppositories and the like.

The invention also provides a method for delivering an oligonucleotide into a cell comprising complexing it with PEI and contacting the complex with the surface of the desired cell. Depending on the type of cell, the molar ratio of PEI nitrogen to oligonucleotide phosphate (N:P ratios) can range from 0.8 to 11.2. In a specific embodiment, a complex of PEI and oligonucleotides of 20 nucleotides with an N:P ratio of 6.4 is delivered into primary blood mononuclear cells.

The invention provides a nucleic acid-polyethylenimine-avidin complex. In specific embodiments, a DNA-polyethylenimine-avidin complex and an oligonucleotide-polyethylenimine-avidin complex are provided.

The invention further provides a cell comprising a covalently linked surface receptor molecule of the invention. Specifically, the cell can be a nucleated blood cell that has biotin molecules covalently linked to its surface. Other cells of the invention include any nucleated cell capable of endocytosis, for example cultured and immortalized cells, primary cells in vivo and ex vivo, and cultured primary cells. In specific embodiments, cells of the invention can be from the liver, breast, heart, lung, epithelium, pancreas, kidney or colon of mammals. In another embodiment, the cell can be a nucleated cell that has a molecule, normally expressed only at low levels on its cell surface, added to its surface through a covalent linkage. The surface receptor can be any of those described herein, those known in the art or those later discovered or developed.

Throughout this application, various publications are referenced. The disclosures of these publications in their entireties are hereby incorporated by reference into this application in order to more fully describe the state of the art to which this invention pertains.

EXAMPLES

Example 1

Methods

A. Biotinylation of Cell Surfaces

1. Direct Biotinylation of Cell Surfaces

Human chronic myelogenous leukemia cells, line K562, are biotinylated as follows: $10^6$ cells are incubated in a final concentration of 0.5 ng sulfo-NHS-Biotin per cell (Pierce Chemicals, Rockford, Ill.) in phosphate buffered saline (PBS) for 30 minutes at 4° C. and washed twice with PBS. For human erythroleukemia (HEL) cells, $5 \times 10^5$ cells are incubated in a final concentration of 1.0 ng sulfo-NHS-Biotin per cell, and for buffy coat cells, $5 \times 10^6$ cells are incubated in a final concentration of 0.1 ng sulfo-NHS-Biotin per cell. After biotinylation, cells are washed with PBS and transferred into 24-well plates in 1.5 ml of adequate cell media. Non-biotinylated cells are used as a control.

Human cells in situ are biotinylated by injecting sulfo-NHS-Biotin into the target tissue or organ at an amount of at least approximately 1 ng per cell. Human blood cells treated ex vivo using apheretic techniques are exposed to sulfo-NHS-Biotin at a concentration of at least approximately 1 ng per cell.

2. Coating of Cells with Biotinylated Antibodies

Biotinylated monoclonal antibodies: antiCD55 (IgG2a), antiCD59 (IgG2a), antiCD71 (IgG2a) and antiCD98 (IgG1) were purchased from Pharmingen (San Diego, Calif.). IgG1 conjugated with FITC and IgG2a conjugated with phycoerythrin (PE) were obtained from Coulter Corporation (Hialeah, Fla.).

For labeling with these biotinylated antibodies, $10^6$ cells were mixed with 20 µl of the antibody in 100 µl PBS, incubated at 4° C. for 30 minutes and washed twice with PBS. Isotypic control staining was performed with 10 µl of IgG1 or IgG2a conjugated with FITC and PE.

B. Cells, Antibodies and Chemicals

K562 human chronic myelogenous leukemia and Jurkat T cell leukemia (clone E6-1) cell lines were obtained from American Type Culture Collection (ATCC) and cultured in the recommended media supplemented with 10% fetal bovine serum (FBS; Diofluids, Rockville, Md.) and with 25 ug/ml gentamicin (Life Technologies, Gaithesburg, Md.).

HEL cells were obtained from ATCC and cultured in RPMI1640 (Biofluids, Inc.) supplemented with 10% FBS. Nucleated cells from the buffy coat were obtained by density centrifugation on ficoll gradients and cultured in phase I media as described (Fibach, E. et al. 1989 Blood 73(1): 100–103).

Cells are counted using a cell counter (Coulter, Fla.). Mouse anti-avidin monoclonal antibody (clone WC19.10, IgG1) conjugated with FITC was from Sigma. IgG1-FITC used for control staining was from Immunotech (Westbrook, Me.). Staining of $10^5$ cells is performed with 4 µl of antibody in 100 µl of PBS for 30 minutes at 4° C. A plasmid DNA encoding an enhanced green fluorescence protein is prepared and purified as described (Mascarenhas, L. et al. 1998 Blood 92(10): 3537–3545; Kain, S R et al. 1998, Methods in Mol. Biol. 102:33–42). Chemicals were purchased from Sigma (St. Louis, Mo.) unless otherwise stated. Sodium periodate was dissolved in water (20 mg/ml) and stored at 25° C. protected from light.

C. Avidin-FITC Addition

Avidin or avidin conjugated with fluorescein isothiocyanate (Av-FITC, 0.1 ng/cell) is incubated with the biotinylated cells (see Example 1A) in 1 ml of PBS. In the time-course studies, cells labeled with Av-FITC are incubated at 37° C. and at each time-point cells are collected, fixed with fresh 2% paraformaldehyde, and analyzed by flow cytometry and fluorescence microscopy.

D. Preparation of PEI-Avidin (PA) Conjugates

Polyethylenimine (PEI; Fluka, Switzerland) of MW 800 kDa was prepared as a 5% w/v hydrochloride salt solution: to 800 µl of commercial PEI (50% w/v water solution) water and 200 µl of 36% hydrochloric acid was added to 8 ml final volume. The pH of prepared PEI was 9.2 and the reagent was stored at 25° C. until used in conjugate preparation. Each avidin sample was prepared by dissolving 20 mg of lyophilized avidin in 2 ml of PBS, pH 7.4. To each sample of dissolved avidin 218 µl of 20 mg/ml sodium periodate solution was added, the sample was wrapped with foil and incubated for 60 minutes at 25° C. The reaction was quenched by gel filtration on Sephadex G-25 superfine (PD10 Pharmacia) column. The resulting 3.5 ml fractions containing protein in PBS, pH 7.4 were used for conjugation with PEI. PEI was added to the avidin fractions at 3 different molar ratios: A—1:4 (60 mg PEI in 1.2 ml), B—1:8 (30 mg PEI in 0.6 ml) and C—1:16 (15 mg PEI in 0.3 ml). The samples were mixed vigorously for 1 hour at 25° C. and 1 ml of coupling buffer (20 mM $Na_3PO_4$, pH7.5, 0.2 M NaCl and 3 mg/ml $NaCNBH_3$) was added to each sample prior to an additional 1 hour incubation. The addition of coupling buffer was repeated twice with a total of 3 ml of coupling buffer added to each sample prior to overnight incubation. Glycine in molar excess quenched the avidin for 1 hour at 25° C. A 10 mm×100 mm Macro-Prep High S support (Bio-Rad, Hercules, Calif.) cation-exchange column equilibrated at 20 mM HEPES, pH 7.5, containing 0.5 M NaCl was used to fractionate the samples with the 0.5–3 M NaCl gradient in 20 mM HEPES, pH 7.5 using a Gilson HPLC system equipped with a protein detection sytem at 280 and 214 nm. Some protein was eluted in the flow-through. The main conjugate fraction of each sample was eluted between 1.3 and 3.0 M salt, pooled, concentrated to 6 ml by ultrafiltration and dialyzed overnight against 3×1 L of PBS, pH 7.4. The avidin content of each conjugate preparation was determined at 280 nm and the PEI content by ninhydrin assay (NIN-SOL ninhydrin reagent from Pierce) at 570 nm. The conjugate reactions yielded the following products: A: 12 mg PEI conjugated to 4.36 mg avidin at the molar ratio of 1:4.36 ("PA4"); B: 3.32 mg PEI conjugated to 2.30 mg avidin at the molar ratio of 1:8.31 ("PA8"), C: 1.05 mg PEI conjugated to 1.35 mg avidin at a molar ration of 1:15.46 ("PA16"). The overall yield of these conjugates based on PEI was: A: 20%, B: 11.7%; C: 7%; based on avidin: A: 21.8%, B: 11.5%, C: 6.75%. The conjugates were aliquoted and stored at −80° C. Gel retardation assay of the PEI conjugates was performed in 1.2% agarose gels as described in Kircheis, R., et al., 1997, Gene Ther. 4:409–418.

E. Transfection of Cells

Plasmid transfection complexes are prepared as follows. Plasmid DNA is added and mixed gently with PEI or PA conjugates in PBS, in a total volume of 0.5 ml. PEI-DNA or PA-DNA complexes are formed at desired molar ratios of PEI nitrogen to DNA phosphate (N:P). Different N:P ratios are prepared by titrating DNA concentrations at a constant PEI concentration or by titrating PEI with the amount of DNA held constant, with the final N:P ratios ranging from 0.8 to 11.2, including 3.2, 4.8, 6.4, and 8. After 30 minutes of incubation at 25° C., 0.5 ml transfection mixture is added to the cells in 1.5 ml culture medium containing 10% FBS and gently mixed. Cultured cells (K562 and Jurkat E6-1) are biotinylated before transfection using standard procedures at 4° C. and washed with cold PBS. After a 4 hour incubation with the transfection complexes, 1 ml fresh culture media containing 15% FBS is added to each well. Transfection is assessed based on GFP expression by fluorescence microscopy and flow cytometry at 24 hours, 2 days, 5, days, 14 days, and 30 days after transfection. GFP encoded by plasmid DNA is a particularly useful marker for successful transfection since endosomal escape, trafficking of plasmid DNA to the nuclear compartment, and high-level protein expression of the transferred gene are required for the cells to fluoresce at detectable levels. GFP expressing cells are defined as those cells having a fluorescence at levels at least two standard deviations above the negative control.

Oligonucleotide transfection complexes are prepared with one of the following oligonucleotides, obtained from Lofstrand Labs Limited (Rockville, Md.): poliT-FL, a 20mer labeled on its 3' and 5' ends with fluorescein; and poliG-FL, a 20mer also labeled on its 3' and 5' ends with fluorescein. The oligonucleotide transfection complexes are prepared as follows: Ten μg of oligonucleotide was added to 0.5 ml PBS containing either 8 μg PEI or 8 μg PA4 (see Example 1.C), giving an N:P ratio of the complex of 6.4. Complexes with lower N:P ratios can be prepared for use, particularly for in in vivo applications, by lowering the amount of PEI or PA4 added so that the N:P ratio results in a complex that is electrophoretically near neutral. After mixing, the transfection media is left for 30 minutes at room temperature, then added to the cells (e.g 0.5 ml transfection media per $5 \times 10^5$ HEL cells or per $5 \times 10^6$ buffy coat cells).

F. Flow Cytometry and Fluorescence Microscopy

Flow cytometry and analyses are performed using an EPICS ELITE ESP flow cytometer (Coulter, Hialeah, Fla.). In each experiment, 10,000 cells are analyzed using argon laser excitation and 525 nM bandpass filtering to detect both FITC fluorescence and GFP expression. Fluorescence microscopy of cells was carried out using an Axiophot microscope (Zeiss, Germany).

Example 2

Avidin-FITC Complexes undergo Endocytosis after Binding to Biotinylated Cells

A. Directly Biotinylated Cells

Untreated K562 cells show very little autofluorescence or nonspecific binding of Av-FITC as assessed by flow cytometry and fluorescence microscopy. When Av-FITC is added to biotinylated K562 cells, Av-FITC is evenly distributed on cell surfaces. Thirty minutes after addition, fluorescein is detected inside endosomal compartments in all cells. The fluorescence gradually shifts from the cell surface to the cell interior during the next 24 hours, which is demonstrated by comparing the fluorescence and phase images of the same microscopic field. The fluorescein remains inside the cells without being recycled to the surface. No internalization is observed when cells are incubated at 4° C., and no exocytosis of fluorescent complexes is detected. A similar pattern and time-course can be observed using K562 and Jurkat cell lines.

Flow cytometry is used to determine whether avidin binding increases the rate of biotin clearance from the cell surface. The level of surface biotin available for avidin binding decreases only 10% over 2 hours in the absence of avidin. A more rapid clearance of surface biotin occurs in the presence of avidin. Within 15 minutes, the surface level decreases sharply by over 20% and only 50% of avidinbound biotin remains after two hours. Av-FITC binding and internalization (endocytosis) causes no significant decrease in cell growth as measured by cell counts. No changes in cells' viability, as measured by dye exclusion, are noticed immediately after Av-FITC internalization or after 3 days, as compared to untreated cells.

B. Cells Coated with Biotinylated Antibodies

Biotinylated antiCD59B antibodies were used initially due to their ability to enter cells after crosslinking to CD59 on the cell surface. In a pattern similar to that observed after direct surface biotinylation (Example 2A), Av-FITC endocytosis was observed following incubation of K562 cells with antiCD59B biotinylated antibody. Immediately after the addition of Av-FITC, all cells displayed well-dispersed surface fluorescence with small areas of increased intensity. Within 24 hours, notable changes in the pattern of fluorescence were recorded. The fluorescence shifted from welldispersed clusters and dots of high intensity on the cell surfaces (capping) to a fluorescence within more localized endosomal compartments in the cell interior. The internalization of Av-FITC was observed in nearly 100% of these cells, analogous to the results in Example 2A. It is also noted that cells form clustered groups directly after avidin labeling, probably as a result of some avidin bridging among neighbor cells. After endocytosis of the surface avidin, the cells no longer showed the tendency to cluster. No internalization of fluorescent complexes occurred when these cells were incubated at 4° C. over the 24 hours period. Untreated cells, cells incubated with isotypic control antibodies, and cells incubated with Av-FITC alone showed no increases in fluorescence as assessed by flow cytometry or fluorescence microscopy. In addition, other leukemic cell lines including HEL and Jurkat cells exhibited a nearly identical pattern and time-course of Av-FITC endocytosis following incubation with biotinylated antiCD59 antibody.

Example 3

PEI-Avidin Conjugates Condense DNA and Efficiently Transfect Cultured Cells

A. Directly Biotinylated Cells

Three PEI-avidin conjugates were prepared with increasing content of avidin as described in the Materials and Methods. PA4, PA8 and PA16 define conjugates with avidin to PEI molar ratios of 4, 8 and 16 respectively. As assessed by gel retardation, cationic binding by PEI and all the PA conjugates completely neutralized the anionic charge of the plasmid DNA to prevent its electrophoresis at the N:P ratio of 3.2. Due to the additional cationic charge of avidin (see Savage, M D et al. 1994, *Avidin-biotin Chemistry: A Handbook*, $2^{nd}$ Ed., Pierce Chemical Co., Rockford, Ill.) and possible differences in the protonation profile of the conjugated PEI, the PA conjugates caused gel retardation at a proportionally lower PEI level. As expected, the PA16 conjugates are most cationic with complete DNA gel retardation at an N:P ratio of 0.8.

Gene transfer efficiencies in K562 and biotinylated K562 cells were determined using the three PA conjugates as a function of N:P ratio and compared with PEI. Two days after transfection, flow cytometry is performed to quantify GFP expressing cells, which are defined as the percentage of cells fluorescing at levels at least two standard deviations above the negative control. PEI-based transfection efficiencies are around 1% among native and biotinylated K562 cells. Control transfection with naked DNA or conjugates lacking DNA were negative. Incorporation of avidin into PEI (the "PA" conjugates) significantly increases transfection efficiency on biotinylated K562 cells.

Cells transfected with PA conjugates at the N:P ratio=6.4 were analyzed over 14 days in culture (Table 1). The transfection efficiencies of all PA conjugates remain significantly higher than that of PEI alone and higher on biotinylated K562 than on corresponding unbiotinylated K562 cells. For each PA conjugate, the transfection efficiencies at all N:P charge ratios increases after target cell biotinylation. Avidin-mediated transfection of biotinylated K562 cells was associated with maximum GFP expression on day 2, as compared to day 5 in unbiotinylated cells. A similar pattern of PA4 transfection is detected using biotinylated Jurkat cells, with 16.7% of the cells expressing GFP after 48 hours.

B. Cells Coated with Biotinylated Antibodies

In the cells coated with biotinylated antiCD59B antibody, PA4-GFP complexes provided a significant increase in transfection efficiency (6.8±0.6%, a 5.2 fold increase) over untargeted PEI-GFP. Three additional biotinylated antibodies, antiCD55B, antiCD71B, and antiCD98B, were also used to direct uptake. The four antigens represented in these experiments have extensive structural differences, but they are all expressed at a consistently high level on hematopoietic cells. While CD59 and CD55 represent GPI-anchored proteins, CD71 and CD98 have transmembrane domains. The transfection efficiency was similar for all biotinylated antibodies tested, with somewhat higher transfection efficiency provided by antiCD71 antibody, which is directed against the transferrin receptor. In all cases, the distribution pattern of GFP expression among individual cells indicated a population of very high level expressing clones.

C. Comparative Analysis of Methods in Examples 3A and 3B

Measurements of the relative level of biotin on the cell surfaces of directly biotinylated cells and cells coated with biotinylated antibodies were made. While biotinylated antiCD59 provides a nine-fold increase in the avidin-FITC fluorescence above the control level (mean fluorescence 11.4 versus the control at 1.27), a 90-fold increase in avidin-FITC fluorescence was observed in directly biotinylated cells (mean fluorescence 110.2). Therefore, the higher transfection efficiency observed after direct biotinylation of the cell surface correlates with a higher level of biotin on the cell surfaces available for PA4 binding.

Example 4

PA4 Mediates Stable Transfection without Growth Selection

FIG. 1 demonstrates both transfection efficiency and the analysis of GFP expression level among individual PA4 transfected cells. Each point in the panels represents a cell with the corresponding GFP expression intensity shown on the y-axis. As shown in FIG. 1A, the transfection efficiency is highest at each logarithmic level with PA4 on biotinylated K562 cells. Over time, the percentage of transfectants expressing GFP at all levels decreased, but the GFP expression remains between 0.1–1.0% after several weeks (FIG. 1B). To examine the stability of GFP expression 30 days after transfection, the upper 0.2% of GFP positive cells were sorted and grown in culture without growth selection for an additional month (FIG. 1C). Analysis on day 10 after sorting shows that over 90% of the cells remain GFP positive. A similar percentage remain positive 20 days later (i.e 60 days after transfection) suggesting PA4 transfection of biotinylated cells results in 0.1–1.0% of cells capable of stable transgene expression in the absence of growth selection.

Example 5

Entry of Fluorescein-Labeled Avidin into Primary Hematopoietic Cells

Biotinylated, freshly isolated peripheral blood cells were analyzed for avidin-FITC uptake in those cells. Immediately upon Av-FITC treatment, 100% of the cells exhibit surface fluorescence. After 24 hours, all the erythrocytes (enucleated cells) remain unchanged with Av-FITC evenly distributed only on their surfaces. In contrast, the fluorescent avidin distribution changes dramatically in mononuclear peripheral blood cells. Unlike the erythrocytes, the pattern of fluorescence among the nucleated blood cells is similar to that observed in cell lines after 24 hours (see Example 2), with nearly 100% of nucleated cells internalizing the fluorescent label. High-power microscopic examination reveals a punctate cytoplasmic distribution in most of the cells. The fluorescent label is also retained at a low level on the plasma membrane of several nucleated blood cells, as compared to the absence of any surface label on the K562 cells after 24 hours.

Example 6

PEI-Avidin conjugates Condense DNA and Transfect Biotinylated Hematopoietic Cell Lines To demonstrate the targeting after endocytosis of molecular conjugates with biological activity in the cytoplasmic and nuclear compartments, avidin-polyetheylenimine (PEI-avidin) bioconjugates were produced to compare with surface receptor-mediated uptake of plasmid DNA using transferrin-polyethylenimine (transferrin-PEI). Four PEI-avidin conjugates were prepared with increasing contents of avidin (see Example 1C). PA2, PA4, PA8 and PA16 define conjugates with avidin to PEI molar ratios of 2, 4, 8 and 16, respectively. Gel retardation assays showed similar profiles of cationic binding by PEI and all the PEI-avidin conjugates to plasmid DNA.

Transfection efficiency of PA4 was measured in hematopoietic cell lines using PEI alone, transferrin-PEI conjugates directed specifically to transferrin receptors, and the non-specific lipid-based reagent DMRIE-C. In untreated or biotinylated cells, the efficiency of transfection of naked DNA or untargeted PEI-DNA is very low, measured as below 1%. Incorporation of avidin into PEI significantly increased transfection efficiency of biotinylated K562, Jurkat and HEL cells to the level achieved with transferrin-PEI. Transfection of cell lines with PA4 and transferrin-PEI conjugates results in a significant increase in GFP expression, when compared to PEI alone, and it results in a several-fold increase when compared to DMRIE-C.

Example 7

PA4-Oligonucleotide and PEI-Oligonucleotide Transfection of HEL and Primary Blood Cells As viewed by fluorescence microscopy, biotinylated HEL cells internalized fluorescein-labeled oligonucleotides after only one hour. In most fluorescing cells, the fluorescence is localized to the cytoplasm or nucleus of the cell. Similarly, primary cells from the buffy coat internalized fluorescein-labeled oligonucleotides after only one hour. The localization in the primary cells is again mostly in the cytoplasm and nuclei.

Example 8

Functional Oligonucleotide Transfer in Primary Cells

RNA-DNA oligonucleotides were used to demonstrate the functional integrity of nucleic acids delivered into cells by the methods described herein. The strategy was to introduce a single nucleotide conversion into the globin locus, which is responsible for changing the wild type $\beta^A$ allele into the sickle cell anemia $\beta^S$ allele in primary cells using specific RNA-DNA oligonucleotides. Introduction of the mutation into erythroid cells should result in the production of hemoglobin S protein in addition to normal hemoglobin A and should be detectable using HPLC.

A. Cells

Primary hematopoietic cells expressing CD34 antigen were purified from fresh blood donation buffy coats from healthy volunteers. For the oligonucleotide transfer, $10^6$ cells were collected, washed twice with PBS and biotinylated. Two biotinylation methods, as described in Examples 1A.1 and 1A.2 herein, were used. The antiCD71 biotinylated monoclonal antibody was used for the cell coating method.

B. Oligonucleotide Complexes

PEI-avidin-oligonucleotide complexes were prepared as follows: 10 µg RNA-DNA oligonucleotide hybrids were added and mixed gently with PEI-avidin (PA4) conjugates at the molar ratios of PEI nitrogen to DNA phosphate (N:P) of 6.4, in D5W, in a total volume of 0.5 ml. After 30 minutes of incubation in 25° C., 0.5 ml of the PEI-avidin-oligonucleotide mixture was gently mixed with the cells in medium. All experiments were performed in 6 well plates (Costar, Cambridge, Mass.), with $10^6$ cells per well. After 4 hours incubation with the PEI-avidin-oligonucleotide complexes, the transfection media over the sitting cells was aspirated and fresh culture media was added to each well.

C. HPLC Analysis

Analysis and separation of hemoglobin variants was done using a Gilson HPLC system equipped with the detection system at 415 nm according to the standard procedure (T. H. J. Huisman, Separation of Hemoglobins and Hemoglobin Chains by HPLC, Journal of Chromatography, 418, 1987, 227–304). Cells for HPLC analysis were lysed by incubation in water on ice followed by two cycles of freezing and sawing. Finally, cell debris was removed by short centrifugation and the supernatant containing cytoplasmic protein fraction was loaded on the cation-exchange, SynChropak CM300 HPLC column (250 mm×4.6 mm). The column was equilibrated in the 30% of buffer A (0.03 Bis-Tris, 0.0015 M KCN, 0.25M sodium acetate, pH 6.3) and 70% of buffer B (0.03M Bis-Tris, 0.0015 m KCN, pH 6.15). Hemoglobin variants were further eluted by formation of a 30%–70% gradient of the buffer A (0.075M–0.175M sodium acetate) in the buffer B, in 30 minutes at room temperature. Eluted protein fractions were collected and stored at −80° C.

D. Assays

Experiments were performed in primary CD34(+) cells stimulated by erythropoietin in culture. Oligonucleotides were transferred on day 1, day 6 and day 12 to assess the transfection potential of the cells at different differentiation stages. Cells were directly biotinylated and oligonucleotide transfer complexes of PA4 with RNA-DNA oligonucleotides were added. Two RNA-DNA oligonucleotides (SC1 and SC2) were tested. SC1 contained the 25 bp sequence identical to that in normal $\beta^A$ hemoglobin chain, whereas SC2 contained the sequence of sickle $\beta^S$ hemoglobin chain (A. Cole-Strauss et al., 1996, Correction of the mutation responsible for sickle cell anemia by an RNA-DNA oligonucleotide, Science 273:1386). All cells after oligonucleotide transfer were cultured for a total of 15 days (14, 8, and 3 days post oligonucleotide transfer, respectively), collected and analyzed by HPLC together with control cells. HPLC analysis of control red blood cells from a homozygous patient suffering from the sickle cell anemia showed the major hemoglobin S peak eluting at 19–25 minutes in the chromatographic process. HPLC analysis of the control red blood cells (day 0) from the healthy donor, whose CD34(+) cells were used in this experiment, detected the major peak for hemoglobin A and some small amounts of other hemoglobin variants including F, $A_{1C}$, and $A_2$. Elution of hemoglobin F was observed at the beginning of the gradient, hemoglobin $A_{1C}$ eluted at 7–10 minutes, hemoglobin A (major peak) at 10–14 minutes, and hemoglobin $A_2$ at 14–18 minutes. No hemoglobin S was detected in this sample. HPLC analysis of the control unmanipulated CD34(+) cells collected on day 1 in culture showed only a trace amount of hemoglobin A. Control unmanipulated cells collected on day 15 in culture expressed hemoglobin A (major peak), as well as small amounts of hemoglobin F, $A_{1C}$, and $A_2$. The overall pattern of hemoglobin peaks was similar to that found in the corresponding red blood cells from the same donor. Again, no hemoglobin S peak was present in this sample. Also, HPLC analysis of cells to which oligonucleotide SC2 was transferred on day 1 and day 6 did not detect any presence of hemoglobin S, while the pattern of other hemoglobin peaks was identical to the control unmanipulated cells collected on day 15 and to the red blood cell sample from the same donor. Analysis of cells to which SC2 oligonucleotide was transferred on day 12 showed a small peak eluting at the time corresponding to the elution time of hemoglobin S, in addition to other hemoglobin variants typically present in the cells after two weeks in culture with erythropoietin. Also, when cells were indirectly biotinylated with biotinylated anti-CD71 antibody followed by PA4-SC2 delivery on day 12, HPLC analysis detected the small peak corresponding to hemoglobin S. No hemoglobin S peak was detected in any of the cell samples targeted with the PA4-SC1 (SC1 is the $\beta^A$ bearing oligonucleotide), while the overall pattern of other hemoglobin peaks was typical. Similar results were obtained in an independent experiment using CD34(+) cells from the second donor.

Although the present invention has been described with reference to specific details of certain embodiments thereof, it is not intended that such details should be regarded as limitations upon the scope of the invention except as and to the extent that they are included in the accompanying claims.

TABLE 1

Transfection efficiency of PEI and PA conjugates in cultured cells. K562 and biotinylated K562 cells were transfected with PEI or PA conjugates complexed with 10 μg pGT at a molar ratio of N:P = 6.4, cultured, and analyzed on day 2, 5, and 14 following transfection. The values in the table are percentages of GFP expressing cells, assessed by flow cytometry from three independent experiments done in duplicate.

| EXPERIMENT | DAY 2 | DAY 5 | DAY 14 |
| --- | --- | --- | --- |
| Control K562 | 0.15 ± 0.05 | 0.20 ± 0.04 | 0.20 ± 0.08 |
| K562 + PEI | 1.60 ± 0.76 | 1.18 ± 0.47 | 0.35 ± 0.13 |
| BK562 + PEI | 1.26 ± 0.80 | 0.66 ± 0.30 | 0.53 ± 0.28 |
| K562 + PA4 | 8.38 ± 1.14 | 9.25 ± 1.54 | 1.63 ± 0.73 |
| K562 + PA8 | 4.05 ± 0.21 | 6.75 ± 0.07 | 1.00 ± 0.00 |
| BK562 + PA16 | 1.85 ± 0.07 | 3.40 ± 1.50 | 2.75 ± 1.34 |
| BK562 + PA4 | 18.04 ± 1.13 | 11.73 ± 1.64 | 1.94 ± 0.55 |

TABLE 1-continued

Transfection efficiency of PEI and PA conjugates in cultured cells. K562 and biotinylated K562 cells were transfected with PEI or PA conjugates complexed with 10 μg pGT at a molar ratio of N:P = 6.4, cultured, and analyzed on day 2, 5, and 14 following transfection. The values in the table are percentages of GFP expressing cells, assessed by flow cytometry from three independent experiments done in duplicate.

| EXPERIMENT | DAY 2 | DAY 5 | DAY 14 |
| --- | --- | --- | --- |
| BK562 + PA8 | 13.78 ± 1.09 | 9.05 ± 1.48 | 1.35 ± 0.21 |
| BK562 + PA16 | 5.00 ± 0.36 | 4.50 ± 0.14 | 2.75 ± 1.34 |

What is claimed is:

1. A method for delivering a protein, enzyme, vitamin, vaccine, transcription factor, hormone, carbohydrate, lipid, or nucleic acid into a cell comprising: 1) covalently linking a molecule to the cell surface, wherein the molecule can act as a surface receptor, 2) complexing the protein, enzyme, vitamin, vaccine, transcription factor, hormone, carbohydrate, lipid, or nucleic acid with a ligand for the surface receptor, and 3) contacting the protein, enzyme, vitamin, vaccine, transcription factor, hormone, carbohydrate, lipid, or nucleic acid-ligand complex with the cell surface, whereby the protein, enzyme, vitamin, vaccine, transcription factor, hormone, carbohydrate, lipid, or nucleic acid is delivered into the cell, wherein the covalently linked molecule is biotin and the ligand is avidin or streptavidin.

2. A composition comprising a nucleic acid-polyethyleneimine-avidin complex, wherein the polyethyleneimine is covalently linked to avidin or streptavidin.

3. The composition of claim 2, wherein the nucleic acid is selected from the group consisting of DNA and oligonucleotide.

* * * * *